US00PP30474P3

(12) United States Plant Patent
Beatson

(10) Patent No.: US PP30,474 P3
(45) Date of Patent: May 7, 2019

(54) HOP PLANT NAMED 'HORT0605'

(50) Latin Name: ***Humulus lupulus* L.**
Varietal Denomination: Hort0605

(71) Applicant: The New Zealand Institute for Plant and Food Research Limited, Auckland (NZ)

(72) Inventor: Ron Beatson, Auckland (NZ)

(73) Assignee: New Zealand Hops Limited, Richmond (NZ)

( * ) Notice: Subject to any disclaimer, the term of this patent is extended or adjusted under 35 U.S.C. 154(b) by 0 days.

(21) Appl. No.: 15/732,309

(22) Filed: Oct. 23, 2017

(65) Prior Publication Data

US 2018/0124975 P1 May 3, 2018

Related U.S. Application Data

(60) Provisional application No. 62/413,724, filed on Oct. 27, 2016.

(51) Int. Cl.
*A01H 5/00* (2018.01)
*A01H 5/02* (2018.01)

(52) U.S. Cl.
USPC ..... Plt./236
CPC ..... *A01H 5/02* (2013.01)

(58) Field of Classification Search
USPC ..... Plt./236
See application file for complete search history.

*Primary Examiner* — Annette H Para
(74) *Attorney, Agent, or Firm* — Leydig, Voit & Mayer, Ltd.

(57) ABSTRACT

A new and distinct hop plant is described. The cultivar results out of selection from a population of seedlings derived from the deliberate crossing the 'Southern Cross' (not patented) and 99-63-31 (not patented). The new variety, 'Hort0605', is characterised by its late maturing and high alpha acid content and low cohumulone content. The new variety is suitable for beer flavouring.

5 Drawing Sheets

Genus and species plant claimed: *Humulus lupulus* L.
Variety denomination: 'HORT0605'.

BACKGROUND OF THE INVENTION

The new cultivar of hop, *Humulus lupulus* L., was created in the course of a planned breeding program carried out at Motueka, New Zealand. It was selected from a population of seedlings derived from a cross made in 2006 between 'Southern Cross' (seed parent) (not patented) and 99-63-31 (pollen parent) (not patented). Seedlings from the cross were grown in a nursery at the same location during the 2006-07 season and subsequently planted in the field in 2007-08 season. In 2008, 'Hort0605' was identified as having potential as a new variety and given the breeder code 06.05-22-02. The cultivar was selected on the basis of its good agronomic performance, and chemistry profile.

SUMMARY OF THE INVENTION

A new and distinct hop plant is described. 'Hort0605' cultivar is characterised by having cones which are late maturing and have high alpha acid and low cohumulone content. The new variety is suitable for beer flavouring.

In 2010/11 'Hort0605' was asexually reproduced in Motueka, New Zealand via rhizome cuttings. The resulting plants were found to be true to type demonstrating that the characteristics of the new variety are stable and transmitted without change through succeeding generations. For two seasons, from 2012/13 to 2013/14 'Hort0605' was trialled, along with three other promising selections and commercial cultivars 'Nelson Sauvin' (not patented) and 'Green Bullet'

(not patented), for its commercial potential. In the winter of 2013 it was decided to advance 'Hort0605' to larger-scale testing.

'Hort0605' is maintained at Motueka, New Zealand, where it has undergone observations for uniformity. All plants have been found to be true to type, that is, no off types have been observed. 'Hort0605' is distinguished from its parent female parent, 'Southern Cross' as 'Hort0605' has stronger anthocyanin coloration on the main shoot and also has higher alpha acid levels. The pollen parent, 99-63-31, is a male and thus does not produce cones. Under New Zealand growing conditions 'Hort0605' is distinguished from varieties of common knowledge by the following characteristics:

When grown in Motueka 'Hort0605' has stronger anthocyanin coloration on the main shoot stem compared to 'Green Bullet' and 'Nelson Sauvin' and is later flowering than either of these varieties.

BRIEF DESCRIPTION OF THE DRAWINGS

The accompanying photographs show typical specimens of the plant habit, cones, and leaves of the new cultivar as depicted in colours as nearly true as is reasonably possible to make the same in colour illustration of this character.

DETAILED DESCRIPTION

Figure 1:
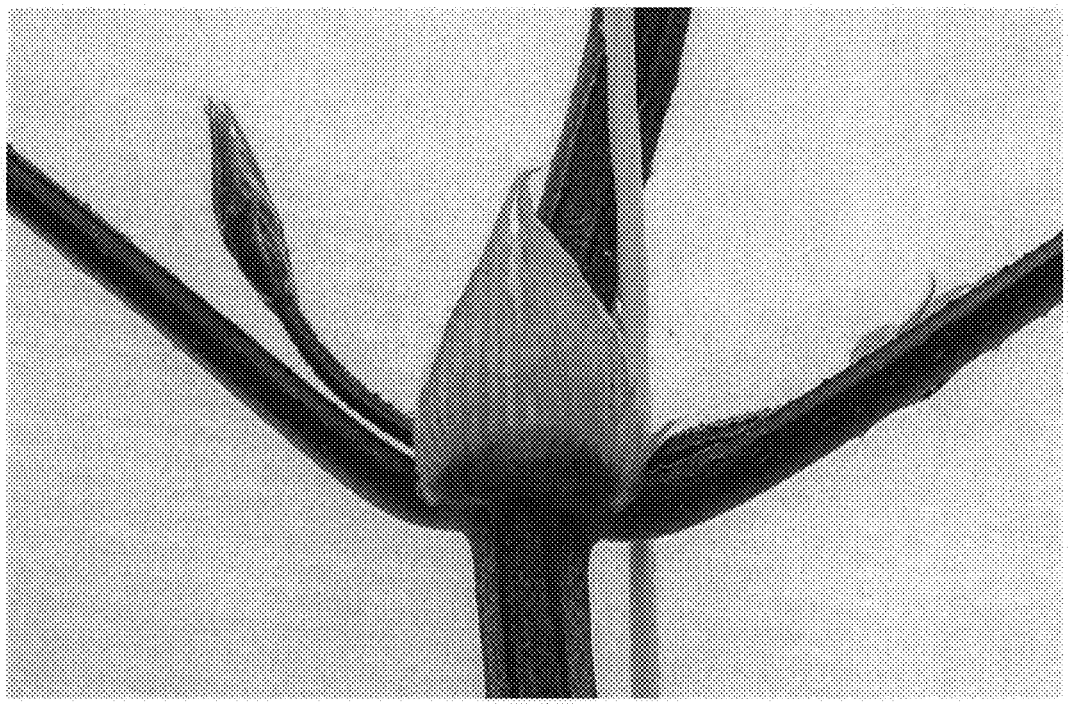
FIG. 1: close up of 'Hort0605' main shoot.
Figure 2:
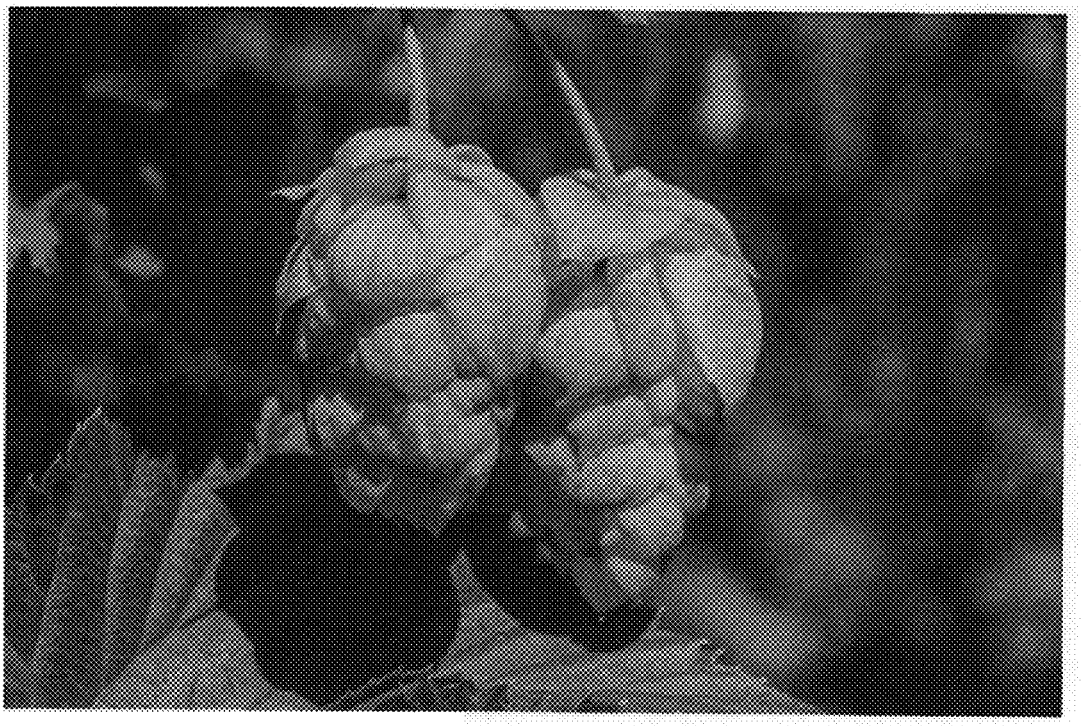
FIG. 2: 'Hort0605' cones in the field.
Figure 3:
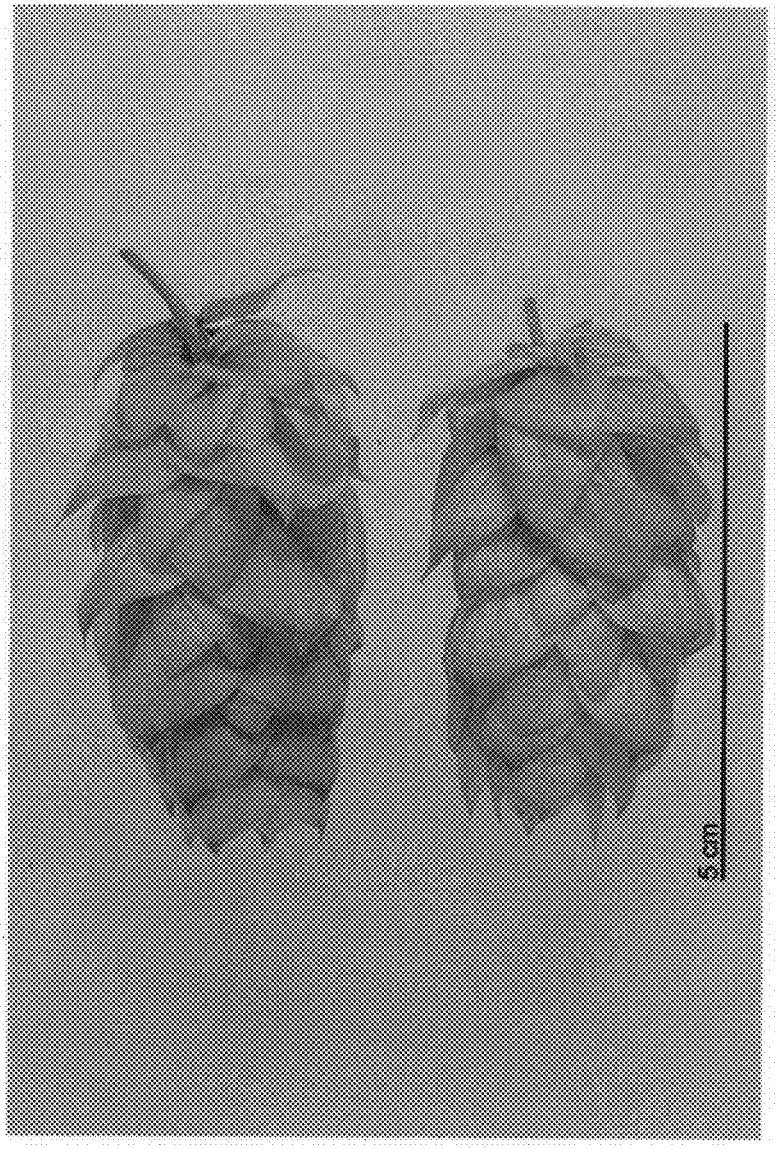
FIG. 3: 'Hort0605' cones in the studio
Figure 4:
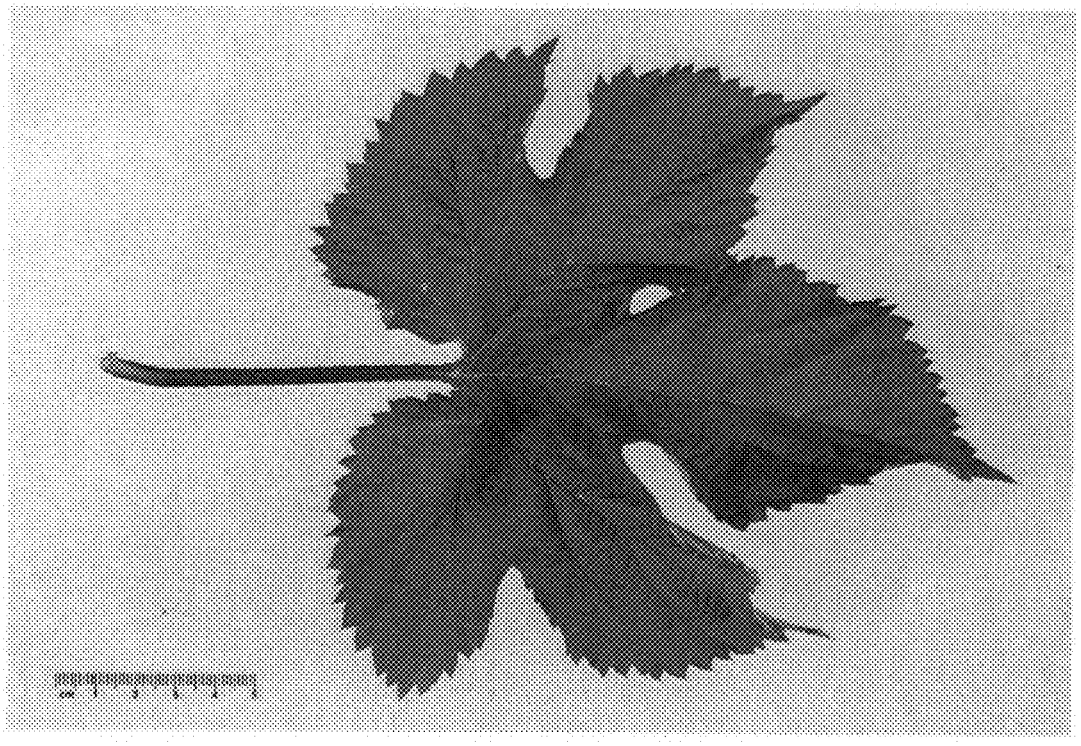
FIG. 4: Upperside of 'Hort0605' leaf
FIG. 5 Mean of at harvest chemistry profiles for 'Hort0605' and two comparator cultivars 'Nelson Sauvin and 'Green Bullet. Trials and testing were conducted in Motueka, New Zealand.
Figure 5:
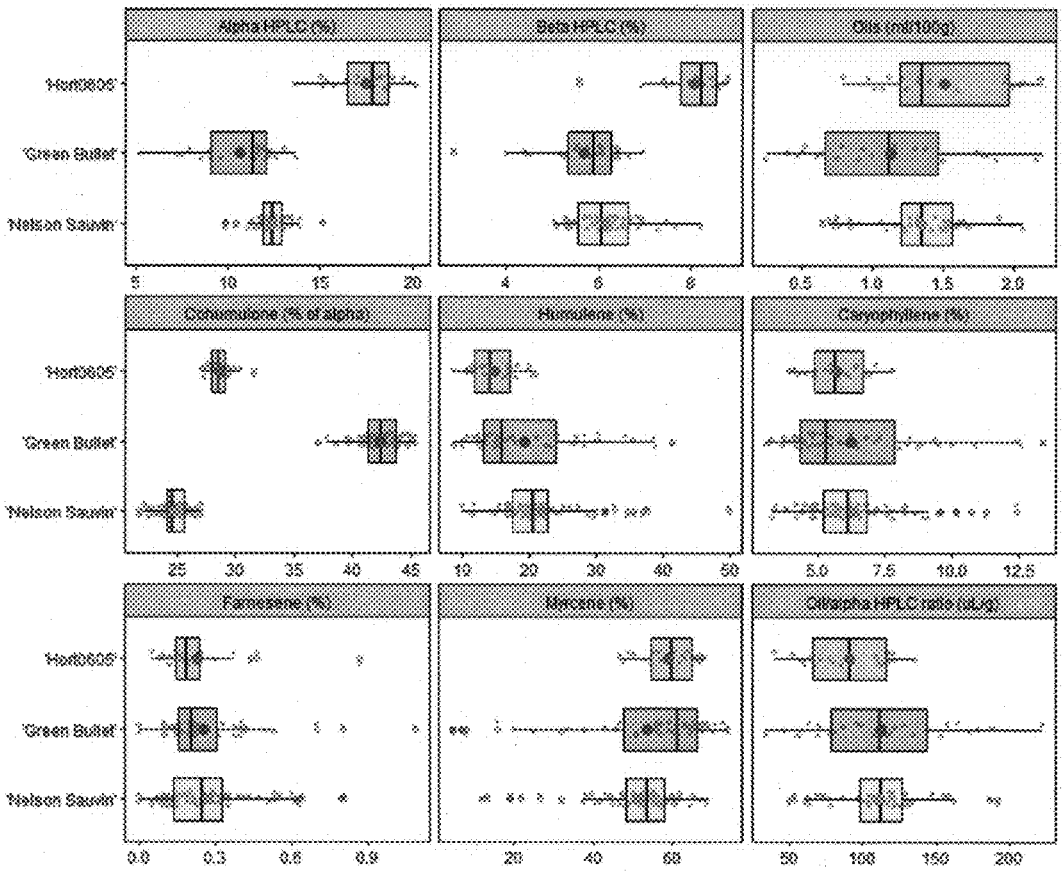

The following is a description of the new cultivar with colour terminology in accordance with The Royal Horticultural Society Colour Charts (R.H.S.C.C.) 2001 edition. The specimens described were grown at Motueka, New Zealand. The observations were made over the 2014-2016 seasons.

Plant form and vigour: Mature plants are of a normal growth type produce a high yield (averaging 2.2-2.8 kg/ha,) of late maturing cones. The main shoot of a one year old plant, has an average vine diameter half way up the vine of 10 mm, and strong anthocyanin coloration, near N79B in color with a stripe present, near Purple, N77A in color. Node pubescence was medium. The average internode length was 200 mm.

Laterals: The side shoots from the middle third of the plant were of long to very long length, an average of approximately 120 cm, and produce a medium number of cones, an average of 5 per node. The side shoots from the top third of the plant had an average length of 100 cm and produced an average of 7 nodes/lateral.

Leaves: The leaves are strongly lobed with predominantly five lobes. The small, weakly blistered leaves are alternate with crenate margins. The upper leaf surface colour is near, Green, 139A. The average leaf size is 120 mm in length and 130 mm in width.

Cones: Are long and medium-ovate in shape in longitudinal section; in cross section they are square in shape. The cones average length is 50 mm and average width 20 mm. Bracts are medium-large in size, with an average length 17 mm and average width 16 mm. Bracteole have an average length are 16 mm and average width 10 mm. Strigs are long, approximately 35 mm, with an average width of 3 mm. The colour of the strig is Green, near N143C.

Physiological timing: Flowering commences late in Motueka, New Zealand around the 26 January. Harvest is late in the New Zealand season, commencing mid to late March, under normal conditions.

Chemistry profile: 'Hort0605' has undergone extensive chemistry profile testing. The chemistry profile of 'Hort0605' differs from both 'Nelson Sauvin' and 'Green Bullet' in a number of ways. It has a lower percentage of columulone compared to 'Green Bullet' and has a higher level of Alpha and Beta acids compared with both 'Green Bullet' and Nelson Savuin'.

Use: Primarily flavouring and bittering ingredient for beer.

Pest and disease: 'Hort0605' does not appear particularly resistant or susceptible to any particular pests or diseases known to afflict *Humulus lupulus*.

Hardiness: The plant cold hardiness according to the American zone classification has not been determined.

The invention claimed is:

1. A new and distinct hop plant substantially as described and illustrated herein.

* * * * *